United States Patent [19]

Nishiyama

[11] Patent Number: 4,564,960
[45] Date of Patent: Jan. 21, 1986

[54] DEVICE FOR FIXING A BELT OF GOGGLES
[76] Inventor: Takashi Nishiyama, 22-4, Ehara-cho, 1-chome, Nakano-ku, Tokyo, Japan
[21] Appl. No.: 584,408
[22] Filed: Feb. 28, 1984
[51] Int. Cl.$^4$ .............................................. A61F 9/02
[52] U.S. Cl. .......................................... 2/452; 24/197
[58] Field of Search ................. 2/452, 439, 440, 441, 2/428, 430, 445, 446, 447, 426; 24/197, 196

[56] References Cited

U.S. PATENT DOCUMENTS 1,515,412 11/1924 Ritter ..................................... 24/197
2,727,237 12/1955 Malcom, Jr. ...................... 2/440 X
2,853,757 9/1958 Rave ..................................... 24/197

FOREIGN PATENT DOCUMENTS 0495468 6/1954 Italy ......................................... 2/439

Primary Examiner—Peter Nerbun
Attorney, Agent, or Firm—Holman & Stern

[57] ABSTRACT

This invention relates to a device for fixing a strap of goggles or a diving mask or the like. The device includes a generally flat strap-securing fitting having a crossbar and fulcruming means extending therefrom.

3 Claims, 4 Drawing Figures

DEVICE FOR FIXING A BELT OF GOGGLES

BACKGROUND OF THE INVENTION

Conventional goggles employ as belt fixing means a buckle. A belt led out from the buckle is inserted into the hole of the body of the goggles, folded, passed at the end through the buckle and fixed while adjusting the length of the belt.

In this structure, the belt can be tightly engaged, but it is complicated to adjust the length of the belt, and is particularly inconvenient by a child to handle the goggles.

It has recently been considered to perforate two holes at the body of the goggles without using a buckle, to pass a belt through the holes and to merely fix the belt by means of the frictional force produced between the holes. However, it is also difficult to adjust the length of the belt in this structure. In addition, it is also difficult to adjust the length of the belt in this structure. Further, the belt feasibly slides by strong tension, and it is inconvenient to move the belt due to the tight engagement of the belt.

SUMMARY OF THE INVENTION

This invention has for its object to provide a device for fixing a belt of goggles which can eliminate the aforementioned disadvantages of the conventional goggles and rapidly and readily adjust the belt.

DESCRIPTION OF THE PREFERRED EMBODIMENT

Figure 1:
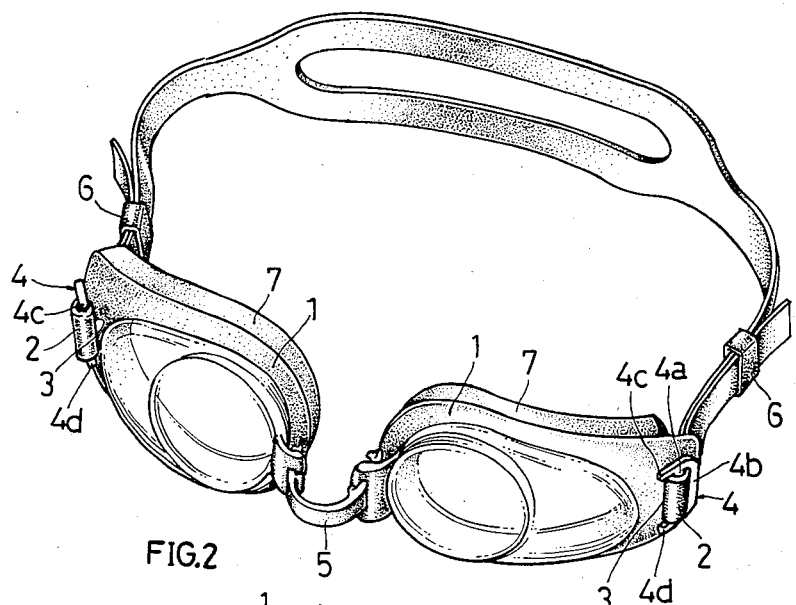
FIG. 1 is a perspective view showing an embodiment of a device for fixing a belt of goggles according to the present invention.

The embodiment of the present invention will now be described in more detail with reference to the accompanying drawings. In this embodiment, shown in FIGS. 1 to 4, a slit 3 of the width, through which a laminated rubber belt 2 can be inserted by means of suitable friction, is formed at each of both right and left ends of a body 1 of goggles, and the belt 2 inserted into the slit 3 is fixed by a fitting 4. The fitting 4 has a rod portion 4a including substantially flat D shape for engaging the belt 2, a frame portion 4b including substantially C shape to form a window hole 4b continued to the vicinity of both ends of the rod portion 4a, and protruding ends 4c, 4d formed at the ends of the frame portion 4b. In this manner, the belt 2 is engaged in U shape with the rod portion 4a of the fitting 4, then inserted at the end into the slit 3 from the front surface of the body 1, and when the belt 2 is then pulled backwardly, the fitting 4 can be pressed to the body 1. It is noted that the fitting 4 of this embodiment is formed entirely in substantially D shape. However, the fitting 4 may be formed with ends 4c and 4d extended to form a closed loop similar to portion 4b. It is accordingly essential that the fitting 4 should have the rod portion 4a at the intermediate, the frame portion 4b' and the upper and lower ends 4c, 4d. It is noted that either one of the rod portion 4a and the frame portion 4b' may be divided in the course. In the drawings, reference numeral 5 designates a joint, 6 designates a band anchoring rod, and 7 designates a face contacting buffer frame of sponge.

Figure 2:
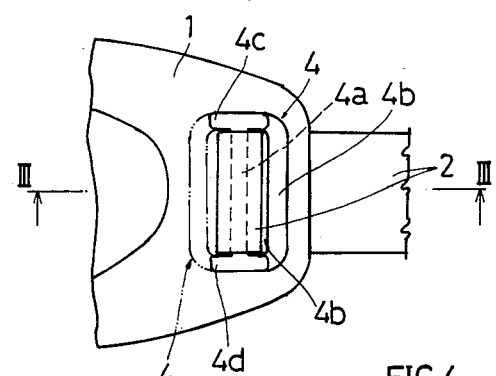
FIG. 2 is a front view of the device.
Figure 3:
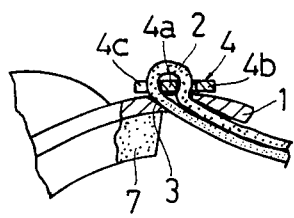
FIG. 3 is a sectional view taken along line III—III in FIG. 2.
Figure 4:
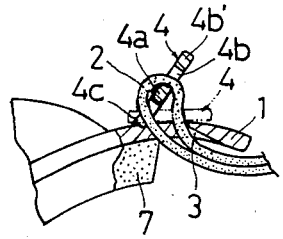
FIG. 4 is a sectional view similar to FIG. 3 for explaining the operation of the device.

In FIG. 2, a chain line shows the inserted fitting 4.

As set forth, according to this invention, when the frame portion 4b' of the fitting 4 is engaged by a finger and the fitting 4 is erected with the protruding ends 4c, 4d of the fitting 4 as fulcra, the belt 2 can be immediately loosened, and when the belt 2 is thereafter pulled, the length of the belt can be freely adjusted. Thus, the belt can be tightly engaged, and is not loosened during use.

What is claimed is:

1. A face mask or goggles structure having a body portion for fitting over a wearer's eyes and a strap attached to opposite ends of the body portion for surrounding the wearer's head, the improvement comprising a strap attachment assembly at least at one end of the body portion, said assembly including a web member formed at said end of the body portion, a slit in the web member, an end portion of the strap being passed through the slit from an inner surface of the web member, a generally flat planar strap-securing fitting unattached to the body portion of the structure, the fitting including a crossbar having a length greater than that of the slit, fulcruming means extending from opposite ends of the crossbar on one side thereof, and finger grip means extending from opposite ends of the crossbar on the other side thereof, the end portion of the strap being looped over the crossbar on an outer surface of the web member and being passed back through the slit whereby the fitting is forced against the outer surface of the web member by tension applied to the strap and wherein the length of the strap may be adjusted by lifting the finger grip means of the fitting away from the outer surface of the web member causing the fulcruming means to turn with respect to the outer surface of the web member so as to raise the crossbar and allow the strap to move lengthwise relative thereof.

2. The invention of claim 1 wherein the fulcruming means comprises finite stub members extending transversely from the opposite ends of the crossbar and wherein the fingergrip means comprises a closed loop portion extending from the opposite ends of the crossbar whereby the fitting has an overall shape substantially in the form of a captial D.

3. The invention of claim 1 wherein the strap attachment assembly is replicated at the other end of the body portion.